US011782258B2

(12) United States Patent
Chen

(10) Patent No.: US 11,782,258 B2
(45) Date of Patent: Oct. 10, 2023

(54) ENDOSCOPIC INSPECTION SYSTEM AND METHOD THEREOF

(71) Applicant: AETHERAI CO. LTD., Taipei (TW)

(72) Inventor: Cheng-Che Chen, New Taipei (TW)

(73) Assignee: aetherAI Co., Ltd., Taipei (TW)

( * ) Notice: Subject to any disclaimer, the term of this patent is extended or adjusted under 35 U.S.C. 154(b) by 288 days.

(21) Appl. No.: 17/284,138

(22) PCT Filed: Jan. 21, 2020

(86) PCT No.: PCT/CN2020/073466
§ 371 (c)(1),
(2) Date: Apr. 9, 2021

(87) PCT Pub. No.: WO2021/146904
PCT Pub. Date: Jul. 29, 2021

(65) Prior Publication Data
US 2022/0148147 A1 May 12, 2022

(51) Int. Cl.
*G06K 9/62* (2022.01)
*G02B 23/24* (2006.01)
(Continued)

(52) U.S. Cl.
CPC .... *G02B 23/2461* (2013.01); *A61B 1/000094* (2022.02); *G02B 23/2484* (2013.01);
(Continued)

(58) Field of Classification Search
CPC ............ G02B 23/2461; G02B 23/2484; A61B 1/000094; A61B 1/04; G06N 3/08;
(Continued)

(56) References Cited

U.S. PATENT DOCUMENTS

2004/0186351 A1* 9/2004 Imaizumi ............... A61B 1/046
600/476
2012/0220823 A1* 8/2012 Choe .................... A61B 1/0684
600/109
(Continued)

FOREIGN PATENT DOCUMENTS

CN 107072511 A 8/2017
CN 109222865 A * 1/2019 ........... A61B 1/0638
(Continued)

OTHER PUBLICATIONS

The Written Opinion and International Search Report for International Application No. PCT/CN2020/073466 dated Oct. 13, 2020.

*Primary Examiner* — Xin Jia
(74) *Attorney, Agent, or Firm* — Haverstock & Owens, A Law Corporation

(57) ABSTRACT

An endoscopic inspection system comprises: a switchable light source device for alternately providing first illumination light and second illumination light to illuminate an inspection location; an endoscope device for acquiring first image data of the inspection location under the illumination of the first illumination light, and acquiring second image data of the inspection location under the illumination of the second illumination light; a processor communicatively connected to the switchable light source device and the endoscope device, wherein the processor determines, according to the first image data and/or the second image data, whether the first image data and/or the second image data contains an abnormal region, and further generates determination data associated with the first image data and/or the second image data; and a display device communicatively connected to the processor for displaying the first image data and the second image data respectively according to a first display instruction and a second display instruction of the processor.

20 Claims, 6 Drawing Sheets

(51) Int. Cl.
*G06N 3/08* (2023.01)
*G06T 7/00* (2017.01)
*A61B 1/00* (2006.01)
*A61B 1/04* (2006.01)

(52) U.S. Cl.
CPC ............ *G06N 3/08* (2013.01); *G06T 7/0002* (2013.01); *A61B 1/04* (2013.01); *G06T 2207/10152* (2013.01); *G06T 2207/20081* (2013.01); *G06T 2207/20084* (2013.01)

(58) Field of Classification Search
CPC .................. G06N 3/045; G06T 7/0002; G06T 2207/10152; G06T 2207/20081; G06T 2207/20084; G06T 2207/10068; G06T 7/0012; G06F 18/00
See application file for complete search history.

(56) References Cited

U.S. PATENT DOCUMENTS

| | | | |
|---|---|---|---|
| 2019/0268538 A1* | 8/2019 | Shiratani | ............ A61B 1/00006 |
| 2020/0008653 A1* | 1/2020 | Kamon | .............. A61B 1/00055 |

FOREIGN PATENT DOCUMENTS

| | | |
|---|---|---|
| CN | 109349987 A | 2/2019 |
| CN | 109447973 A | 3/2019 |
| CN | 110232408 A | 9/2019 |
| WO | WO-2019030749 A1 * | 2/2019 ......... A61B 1/00006 |

* cited by examiner

ENDOSCOPIC INSPECTION SYSTEM AND METHOD THEREOF

TECHNICAL HELD

The present invention relates to an endoscopic inspection system for abnormality inspection and a method thereof, and particularly, relates to an endoscopic inspection system for abnormality inspection alternatively switching between different illumination light and a method thereof.

BACKGROUND

The conventional endoscopic inspection system can provide white light or narrow band imaging (NBI) light according to operations of a user. When the user chooses to perform operations under white light, the endoscopic inspection system will only perform detection to obtain white light image data. In this situation, when the user uses a white light mode, if no abnormal region is found in the currently obtained white light image, the user will not realize that it is necessary to switch to an NBI light mode to further determine the category of the abnormal region. Thus, a high-risk abnormal region could be possibly overlooked by the user. In view of this, there is a need for an endoscopic inspection system for abnormality inspection and a method thereof, which can provide image data obtained under one kind of illumination light for a user to view while performing detection to obtain image data under other kinds of illumination light at the same time, and further determine whether there is an abnormal region in the image data according to the obtained image data.

SUMMARY

In order to solve the above problem, one scheme of the present invention is to provide an endoscopic inspection system for abnormality inspection and a method thereof, which can provide image data obtained under one kind of illumination light for a user to view while performing detection to obtain image data under other kinds of illumination light at the same time, and further determine whether there is an abnormal region in the image data according to the obtained image data.

On the basis of the disclosed scheme, the present invention provides an endoscopic inspection system, comprising: a switchable light source device for alternately providing first illumination light and second illumination light to illuminate an inspection location; an endoscope device for acquiring first image data of the inspection location under the illumination of the first illumination light, and acquiring second image data of the inspection location under the illumination of the second illumination light; a processor communicatively connected to the switchable light source device and the endoscope device, wherein the processor determines, according to the first image data and/or the second image data, whether the first image data and/or the second image data contains an abnormal region, and further generates determination data associated with the first image data and/or the second image data; and a display device communicatively connected to the processor for displaying the first image data and the second image data respectively according to a first display instruction and a second display instruction of the processor.

In one preferred embodiment of the present invention, the first illumination light is white light, and the second illumination light is narrow band imaging (NM) blue light or NBI green light.

In one preferred embodiment of the present invention, the switchable light source device alternately provides the first illumination light and the second illumination light at a switching frequency greater than 30 Hz.

In one preferred embodiment of the present invention, if the processor determines that the first image data and/or the second image data contains an abnormal region, the display device is instructed to mark the abnormal region on the first image data and/or the second image data according to the determination data.

In one preferred embodiment of the present invention, the determination data comprises probability data, and when marking the abnormal region on the first image data and/or the second image data, the display device displays the probability data on the first image data and/or the second image data at the same time.

In one preferred embodiment of the present invention, the determination data comprises a type label associated with the first image data, the second image data, or the abnormal region.

In one preferred embodiment of the present invention, if the processor determines that the first image data and/or the second image data contains an abnormal region, the processor issues an alert signal.

In one preferred embodiment of the present invention, the processor comprises a convolutional neural network module, wherein the processor determines whether the first image data and/or the second image data contains an abnormal region by means of the convolutional neural network module, and further generates the determination data.

In one preferred embodiment of the present invention, the processor comprises a training module, and the training module trains the convolutional neural network module by means of a plurality pieces of training data; wherein each of the plurality pieces of training data is associated with a type label.

In one preferred embodiment of the present invention, the processor comprises a training module, and the training module acquires target region data from the first image data and/or the second image data according to a control instruction; wherein the training module associates the target region data with a type label according to a first determination instruction; wherein the training module trains the convolutional neural network module by means of the target region data associated with the type label.

In one preferred embodiment of the present invention, the processor comprises a training module, and the training module associates the first image data and/or the second image data with a type label according to a second determination instruction; wherein the training module trains the convolutional neural network module by means of the first image data and/or the second image data associated with the type label.

According to the objective of the present invention, an endoscopic inspection method is further provided, the method comprising: alternately providing, by a switchable light source device, first illumination light and second illumination light to illuminate an inspection location; acquiring, by an endoscope device, first image data of the inspection location under the illumination of the first illumination light, and acquiring second image data of the inspection location under the illumination of the second illumination light; determining, according to the first image data and/or the second image data by a processor communicatively connected to the switchable light source device and the endoscope device, whether the first image data and/or the second image data contains an abnormal region, and further generating determination data; associating, by the processor, the determination data with the first image data and/or the second image data; and displaying, by a display device communicatively connected to the processor, the first image data and the second image data respectively according to a first display instruction and a second display instruction of the processor.

In one preferred embodiment of the present invention, the first illumination light is white light, and the second illumination light is NBI blue light or NBI green light.

In one preferred embodiment of the present invention, the switchable light source device alternately provides the first illumination light and the second illumination light at a switching frequency greater than 30 Hz.

In one preferred embodiment of the present invention, the endoscopic inspection method for abnormality inspection further comprises: if the processor determines that the first image data and/or the second image data contains an abnormal region, instructing, by the processor, the display device to mark the abnormal region on the first image data and/or the second image data according to the determination data.

In one preferred embodiment of the present invention, the determination data comprises probability data, and when marking the abnormal region on the first image data and/or the second image data, the display device displays the probability data on the first image data and/or the second image data at the same time.

In one preferred embodiment of the present invention, the determination data comprises a type label associated with the first image data, the second image data, or the abnormal region.

In one preferred embodiment of the present invention, the endoscopic inspection method for abnormality inspection further comprises: if the processor determines that the first image data and/or the second image data contains an abnormal region, the processor issues an alert signal.

In one preferred embodiment of the present invention, the processor comprises a convolutional neural network module, wherein the processor determines whether the first image data and/or the second image data contains an abnormal region by means of the convolutional neural network module, and further generates the determination data.

In one preferred embodiment of the present invention, the endoscopic inspection method for abnormality inspection further comprises: training, by a training module of the processor, the convolutional neural network module by means of a plurality pieces of training data; wherein each of the plurality pieces of training data is associated with a type label.

In one preferred embodiment of the present invention, the endoscopic inspection method for abnormality inspection further comprises: acquiring, by a training module of the processor, target region data from the first image data and/or the second image data according to a control instruction; associating, by the training module, the target region data with a type label according to a first determination instruction; and training, by the training module, the convolutional neural network module by means of the target region data associated with the type label.

In one preferred embodiment of the present invention, the endoscopic inspection method for abnormality inspection further comprises: associating, by a training module of the processor, the first image data and/or the second image data with a type label according to a second determination instruction; and training, by the training module, the convolutional neural network module by means of the first image data and/or the second image data associated with the type label.

The foregoing aspects and other aspects of the present invention will become apparent in accordance with the detailed description of the following non-limitative particular embodiments and with reference to the accompanying drawings.

DESCRIPTION OF EMBODIMENTS

Figure 1:
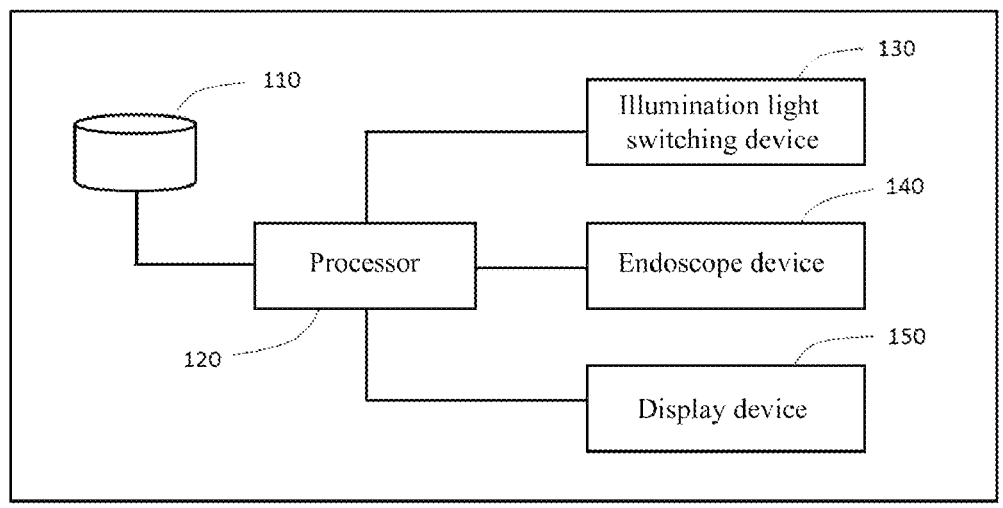
FIG. 1 is a system architecture diagram of a particular embodiment of an endoscopic inspection system of the present invention.

Referring to FIG. 1, a system architecture diagram according to a particular embodiment of an endoscopic inspection system of the present invention is exemplarily illustrated. As shown in the embodiment illustrated in FIG. 1, the endoscopic inspection system 100 comprises a database 110, a processor 120, a switchable light source device 130, an endoscope device 140, and a display device 150. The processor 120 is communicatively connected to the database 110, the switchable light source device 130, the endoscope device 140, and the display device 150. The switchable light source device 130 alternately provides first illumination light and second illumination light to illuminate an inspection location. The endoscope device 140 can acquire (or perform detection to obtain) first image data of the inspection location under the illumination of the first illumination light, and acquire (or perform detection to obtain) second image data of the inspection location under the illumination of the second illumination light. The processor 120 can determine, according to the first image data and/or the second image data, whether the first image data and/or the second image data contains an abnormal region, and the processor 120 further generates determination data associated with the first image data and/or the second image data according to a determination result. If determining that the first image data and/or the second image data contains an abnormal region, the processor 120 can also issue an alert signal. In addition, the processor 120 can also store the first image data, the second image data, and the determination data acquired (or obtained) by the endoscope device 140 to the database 110. The display device 150 can display the first image data according to a first display instruction, and can display the second image data according to a second display instruction. Hence, a user can choose to view the first image data or the second image data according to requirements. In other particular embodiments, the alert signal may be a sound, light, an image, or the like, but is not limited thereto. It should be understood that the abnormal region comprised in the first image data and/or the second image data corresponds to (or represents) an abnormal region on the inspection location. In a particular embodiment, the inspection location is the digestive tract (e.g., the large intestine), and the abnormal region is a polyp.

It should be understood that because the switchable light source device 130 continuously switches between the first illumination light and the second illumination, when the user is viewing the first image data, the endoscopic inspection device 140 can still acquire (or perform detection to obtain) the second image data when the switchable light source device 130 switches to the second illumination light. Similarly, when the user is viewing the second image data, the endoscopic inspection device 140 can still acquire (or perform detection to obtain) the first image data when the switchable light source device 130 switches to the first illumination light. Hence, no matter whether the user chooses to view the first image data or the second image data, the endoscopic inspection device 140 can continuously acquire (or perform detection to obtain) the first image data and the second image data for the processor 120 to perform determination.

It should be understood that when the user is viewing the first image data or the second image data, the processor 120 performs abnormal region determination on the first image data and/or the second image data in a substantially synchronized manner. Hence, the endoscopic inspection system 100 enables the user to be aware of whether the currently obtained first image data and/or the second image data contains an abnormal region by means of the alert signal and/or the determination data, while the user obtains the first image data or the second image data by means of detection performed by the endoscope device 140. In this way, the user can perform an appropriate treatment on the abnormal region immediately (e.g., immediate removal or no treatment at that time). In a particular embodiment, the determination data comprises a type label. The type label is associated with the first image data and/or the second image data, and indicates that the first image data and/or the second image data is an image of a normal region (that is, no abnormal region is comprised). In a particular embodiment, the type label is associated with the first image data and/or the second image data, and indicates that the first image data and/or the second image data is an image comprising the abnormal region. In a particular embodiment, the type label is associated with a target region in the first image data and/or the second image data, and indicates the category of the target region (e.g., the target region is a normal region or an abnormal region). If the abnormal region comprises different kinds of abnormal regions, the type label indicates which kind of abnormal region the target region is.

In a particular embodiment, the first illumination light is white light, and the second illumination light is narrow band imaging (NBI) light. In other particular embodiments, the NBI light is NBI blue light or NM green light, but is not limited thereto. In a particular embodiment, the switchable light source device 130 alternately provides the first illumination light and the second illumination light at a switching frequency. In a particular embodiment, since the switching frequency is high enough, when the user chooses to view the first image data, the displayed first image data is visually continuous images. When the user chooses to view the second image data, the displayed second image data is also visually continuous images. In a particular embodiment, the switching frequency is greater than 30 Hz because when the switching frequency is less than 30 Hz, the image capture frequency of the first image data and the image capture frequency of the second image data will be less than 15 Hz, which will make the images not visually continuous. In a particular embodiment, the switching frequency is less than 240 Hz. In a particular embodiment, the switching frequency is 60 Hz. Hence, the image capture frequency of the first image data and the image capture frequency of the second image data will be 30 Hz. It should be understood that the switching frequency is not limited to 60 Hz, and can be configured to be other values as required. In a particular embodiment, the switching frequency may be configured by the user himself.

In a particular embodiment, the switchable light source device 130 has first illumination light source and second illumination light source. The switchable light source device 130 respectively provides the first illumination light and the second illumination light by switching the first illumination light source and the second illumination light source. In a particular embodiment, the switchable light source device 130 only has a single light source (e.g., a white light source, but not limited thereto) and a light filtering device. The switchable light source device 130 switches the first illumination light and the second illumination light by manipulating the light filtering device. In a particular embodiment, illumination light provided by the single light source is the first illumination light, and illumination light generated after the filtering of the light filtering device is the second illumination light. In another particular embodiment, the light filtering device has two light filtering portions; illumination light generated after the filtering of the first filtering portion is the first illumination light, and illumination light generated after the filtering of the second filtering portion is the second illumination light.

In a particular embodiment, if the processor 120 determines that the first image data and/or the second image data contains the abnormal region, the display device 150 is instructed to mark the abnormal region on the first image data and/or the second image data according to the determination data. The marking method may comprise, but is not limited to, for example, indicating the position of the abnormal region, or marking the contour or the boundary of the abnormal region on the first image data and/or the second image data.

In a particular embodiment, the determination data comprises probability data. The probability data is acquired by the determination of the processor 120 according to the first image data and/or the second image data. In a particular embodiment, the probability data represents the probability that the abnormal region determined by the processor 120 is indeed an abnormal region. In a particular embodiment, the probability data represents the probability that the first image data and/or the second image data indeed do not contain an abnormal region. When marking the abnormal region on the first image data and/or the second image data, the display device 150 can display the probability data on the first image data and/or the second image data at the same time.

Figure 2:
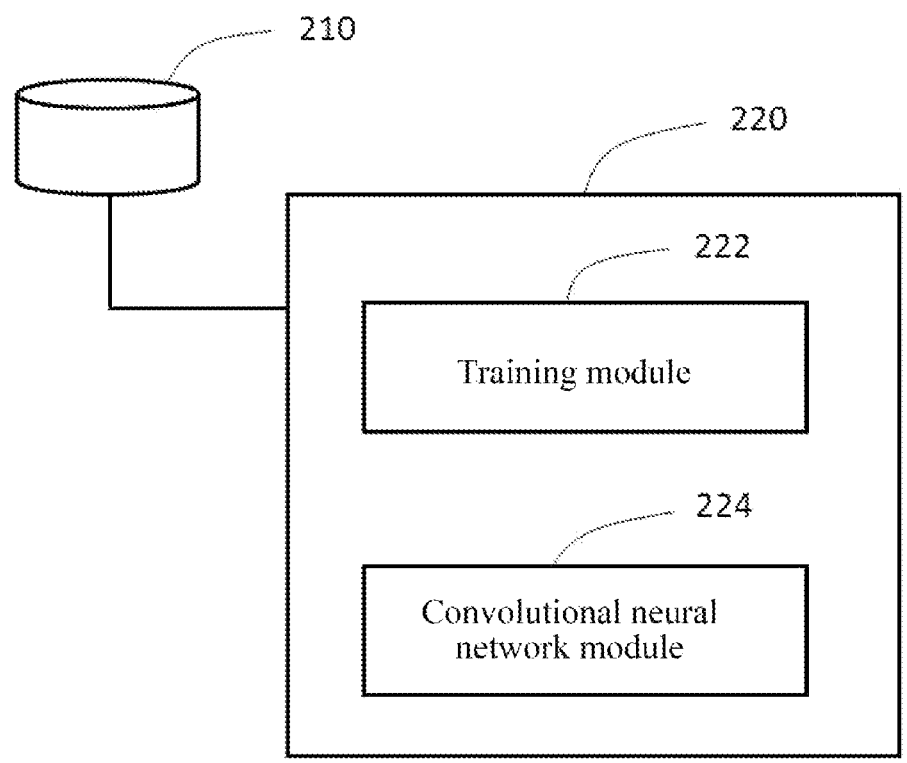
FIG. 2 is an architecture diagram of a particular embodiment of a processor of the endoscopic inspection system of the present invention.

Referring to FIG. 2, an architecture diagram of a particular embodiment of the processor of the endoscopic inspection system of the present invention is exemplarily illustrated. As shown in the embodiment illustrated in FIG. 2, the processor 220 is communicatively connected to the database 210. The database 210 stores a plurality pieces of training data, and each of the plurality pieces of training data is associated with a type label. The type label of respective training data records the type of the content of the training data.

In a particular embodiment, the endoscopic inspection system is used to determine whether there is a polyp (the polyp represents the abnormal region) in the digestive system. The used training data comprise image data of normal regions in the digestive system and image data of polyps in the digestive system. The processor 220 can determine whether the training data is the image data of the normal region or the image data of the polyp according to the type label associated with respective training data. In another particular embodiment, the endoscopic inspection system is used to determine whether there is a polyp in the digestive system (no matter what the category of the polyp is, the polyp represents a kind of abnormal region), and the category of the polyp (e.g. a hyperplastic polyp or an adenomatous polyp). The used training data comprise image data of normal regions in the digestive system, image data of a first category of polyps (e.g., hyperplastic polyps) in the digestive system, and image data of a second category of polyp (e.g. adenomatous polyp) in the digestive system. The processor 220 can determine whether the training data is the image data of the normal region, the image data of the first category of polyp, or the image data of the second category of polyp according to the type label associated with respective training data.

In the embodiment shown in FIG. 2, the processor 220 comprises a training module 222 and a convolutional neural network module 224. The processor 220 can train the convolutional neural network module 224 by means of the training module 222. Hence, the processor 220 can determine whether the first image data and/or the second image data comprise(s) an abnormal region by means of the convolutional neural network module 224, and further generate the determination data. The training module 222 trains the convolutional neural network module 224 by means of the plurality pieces of training data stored in the database 210, and each of the plurality pieces of training data is associated with a type label. In a particular embodiment, the processor 220 implements the training module 222 and the convolutional neural network module 224 in a manner of coordinated operation of hardware and software.

In a particular embodiment, the user can perform determination with respect to the first image data and/or the second image data by himself, and can store the first image data and/or the second image data into the database 210 as one of the training data after the determination. A determination result made by the user for the first image data and/or the second image data is the type label of the first image data and/or the second image data.

In a particular embodiment, the user can mark the boundary or the contour of a target region (e.g., an abnormal region) on the first image data and/or the second image data by providing a control instruction. Hence, the training module 222 can acquire target region data from the first image data and/or the second image data according to the control instruction. The training module 222 can then associate the target region data with a type label according to a first determination instruction provided by the user. The type label is the result of determination made by the user for the target region, which indicates whether the target region is a normal region or an abnormal region (if the abnormal region comprises different kinds of abnormal regions, the type label can indicate which kind of abnormal region the target region is). The training module 222 can also train the convolutional neural network module 224 by means of the target region data associated with the type label.

In a particular embodiment, if the user determines that the first image data and/or the second image data does not comprise the abnormal region and is an image of a normal region, the training module 222 can associate the first image data and/or the second image data with a type label according to a second determination instruction provided by the user. The type label is the determination result of the user for the first image data and/or the second image data. It should be understood that if the user determines that the first image data and/or the second image data contains the abnormal region, the user can also choose to directly associate the first image data and/or the second image data with a type label without marking the boundary of the abnormal region on the first image data and/or the second image data in advance.

Figure 3:
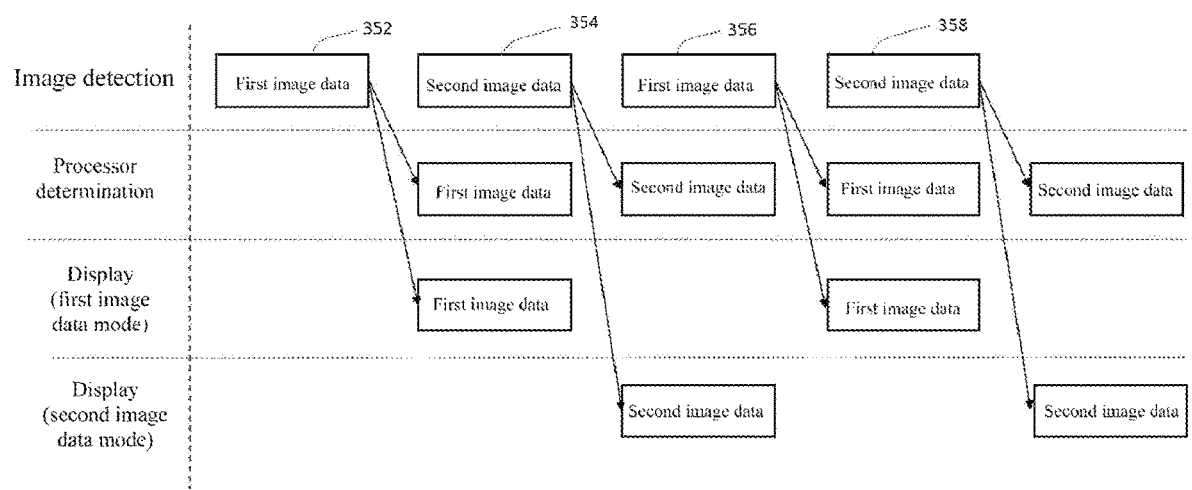
FIG. 3 is a schematic diagram of a particular embodiment of the endoscopic inspection system of the present invention.

Referring to FIG. 3, a schematic diagram of a particular embodiment of the endoscopic inspection system of the present invention is shown. As shown in the embodiment illustrated in FIG. 3, since the switchable light source device alternately provides the first illumination light and the second illumination light, the endoscope device can sequentially perform detection to obtain the first image data 352, the second image data 354, the first image data 356, and the second image data 358. After the endoscope device performs detection to obtain the first image data 352 and 356 respectively, the first image data 352 and 356 are then handed over to the processor for determination. In addition, if the user chooses to view the first image data, while the processor performs determination with respect to the first image data 352 and 356, the first image data 352 and 356 are also provided for viewing by the user by means of the display device at the same time. Because the switching frequency of the switchable light source device is high enough, the first image data 352 and 356 are visually continuous images. Similarly, after the endoscope device performs detection to obtain the second image data 354 and 358 respectively, the second image data 354 and 358 are then handed over to the processor for determination. In addition, if the user chooses to view the second image data, while the processor performs determination with respect to the second image data 354 and 358, the second image data 354 and 358 are also provided for viewing by the user by means of the display device at the same time. Because the switching frequency of the switchable light source device is high enough, the second image data 354 and 358 are visually continuous images.

Figure 4:
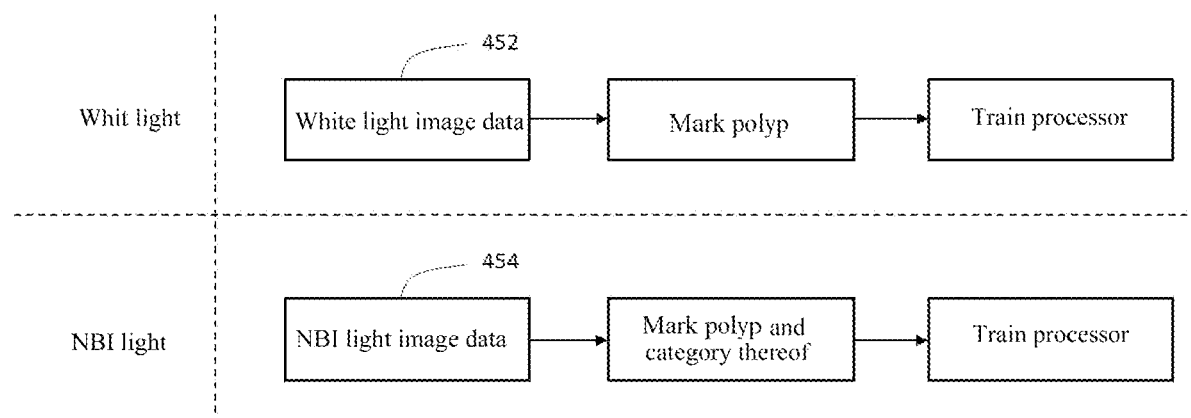
FIG. 4 is a schematic diagram of a particular embodiment of training the processor.

Referring to FIG. 4, a schematic diagram of a particular embodiment of training the processor is shown. As shown in the embodiment illustrated in FIG. 4, the first illumination light is white light, and the second illumination light is NBI light. The first image data is white light image data, and the second image data is NBI image data. When white light image data 452 is obtained, the user can mark the white light image data 452 to indicate whether there is a polyp, and then the processor is trained by means of the white light image data 452 comprising the mark. In a particular embodiment, when marking a polyp, the user can further mark the position of the polyp and/or the boundary thereof. In a particular embodiment, when marking a polyp, the user can further mark the category of the polyp. In a particular embodiment, the processor comprises an artificial intelligence module (e.g., a convolutional neural network module). In addition, As shown in the embodiment illustrated in FIG. 4, when NBI light image data 454 is obtained, the user can mark the NBI light image data 454 to indicate whether there is a polyp, and indicate the category of the polyp (e.g., a hyperplastic polyp or an adenomatous polyp), and then the processor is trained by means of the NBI light image data 454 comprising the marks. In a particular embodiment, when marking a polyp, the user can further mark the position of the polyp and/or the boundary thereof. It should be understood that no matter what category the polyp is, it represents a kind of abnormal region. An abnormal region comprised in image data is a region corresponding to the polyp in the image data.

Figure 5:
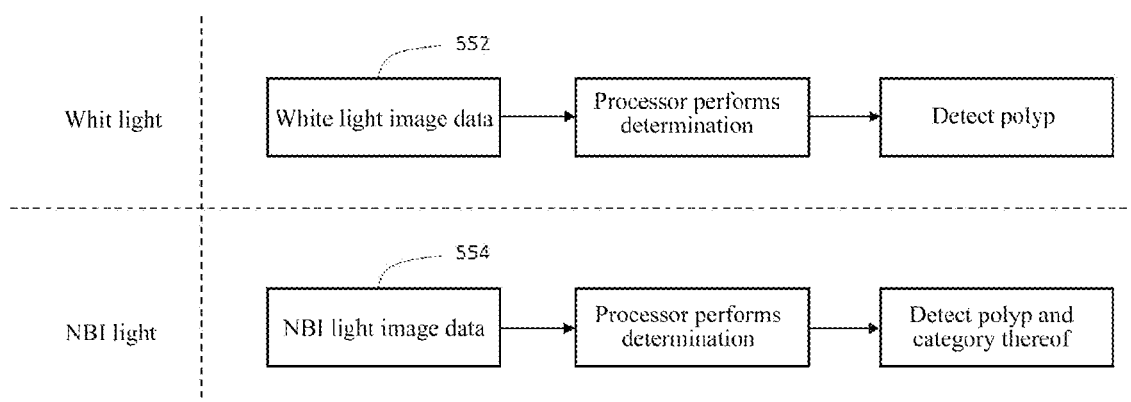
FIG. 5 is a schematic diagram of a particular embodiment of using the processor to perform determination.

Referring to FIG. 5, a schematic diagram of a particular embodiment of using the processor to perform determination (or deduction) is shown. As shown in the embodiment illustrated in FIG. 5, the first illumination light is white light, and the second illumination light is NBI light. The first image data is white light image data, and the second image data is NBI image data. When white light image data 552 is obtained, the processor can determine (or deduce) whether there is a polyp thereon according to the white light image data 552. When NBI light image data 554 is obtained, the processor can determine (or deduce) whether there is a polyp thereon according to the NBI light image data 554, and further determine (or deduce) the category of the polyp. In a particular embodiment, the processor comprises an artificial intelligence module (e.g., a convolutional neural network module), and the processor performs image data determination (or known as deduction) by means of the artificial intelligence module. In a particular embodiment, the processor can further determine (or deduce) the category of a polyp according to the white light image data 552. It should be understood that no matter what category the polyp is, it represents a kind of abnormal region.

Figure 6:
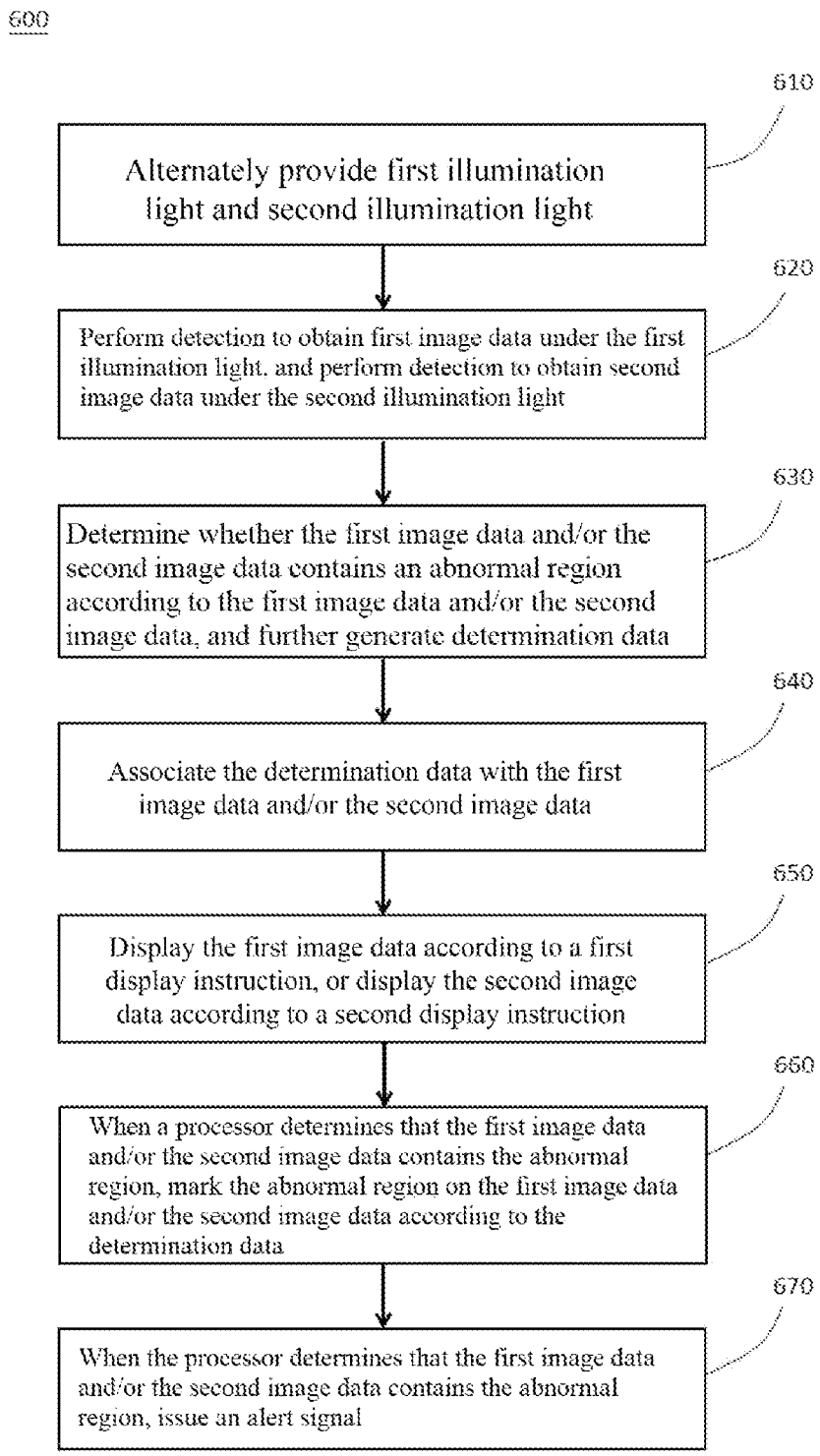
FIG. 6 is a flowchart of a particular embodiment of an endoscopic inspection method of the present invention.

Referring to FIG. 6, a flowchart of a particular embodiment of an endoscopic inspection method of the present invention is exemplarily illustrated. As shown in the embodiment illustrated in FIG. 6, the endoscopic inspection method 600 is applied to an endoscopic inspection system, and the endoscopic inspection system comprises a switchable light source device, an endoscope device, a processor, and a display device. The endoscopic inspection method 600 starts from step 610; the switchable light source device alternately provides first illumination light and second illumination light to illuminate an inspection location. In a particular embodiment, the first illumination light is white light, and the second illumination light is NBI light. In other particular embodiments, the NBI light is NBI blue light or NBI green light, but is not limited thereto.

After performing step 610, step 620 is then performed; the endoscope device acquires (or performs detection to obtain) first image data under the illumination of the first illumination light, and acquires (or performs detection to obtain) second image data under the illumination of the second illumination light. Then, step 630 is performed; the processor communicatively connected to the switchable light source device and the endoscope device determines, according to the first image data and/or the second image data, whether the first image data and/or the second image data contains an abnormal region, and further generates determination data. In a particular embodiment, the determination data comprises a type label, wherein the type label is associated with the first image data, the second image data, or the abnormal region.

After performing step 630, step 640 is then performed; the processor associates the determination data with the first image data and/or the second image data. Then, step 650 is performed; the display device communicatively connected to the processor respectively displays the first image data and the second image data according to a first display instruction and a second display instruction of the processor. In a particular embodiment, the switchable light source device alternately provides the first illumination light and the second illumination light at a switching frequency. Since the switching frequency is high enough, when the user chooses to view the first image data, the displayed first image data is visually continuous images. When the user chooses to view the second image data, the displayed second image data is also visually continuous images. In a particular embodiment, the switching frequency is 60 Hz.

After performing step 650, step 660 is then performed; if the processor determines that the first image data and/or the second image data contains an abnormal region, the processor instructs the display device to mark the abnormal region on the first image data and/or the second image data according to the determination data. In a particular embodiment, the determination data comprises probability data, and when marking the abnormal region on the first image data and/or the second image data, the display device can display the probability data on the first image data and/or the second image data at the same time. In a particular embodiment, the probability data represents the probability that the abnormal region determined by the processor is indeed an abnormal region. In a particular embodiment, the probability data represents the probability that the first image data and/or the second image data indeed do not contain an abnormal region. Finally, step 670 is performed; if the processor determines that the first image data and/or the second image data contains an abnormal region, the processor issues an alert signal.

It should be understood that in other particular embodiments, the order of step 630 to step 670 can be adjusted according to requirements. In a particular embodiment, the processor of the endoscopic inspection system comprises a convolutional neural network module and a training module. The processor determines whether the first image data and/or the second image data contains an abnormal region by means of the convolutional neural network module, and further generates the determination data. In a particular embodiment, the endoscopic inspection method 600 further comprises: the training module of the processor training the convolutional neural network module by means of a plurality pieces of training data. Each of the plurality pieces of training data is associated with a type label.

In a particular embodiment, the endoscopic inspection method 600 further comprises: the training module acquiring target region data from the first image data and/or the second image data according to a control instruction; the training module associating the target region data with a type label according to a first determination instruction; and the training module training the convolutional neural network module by means of the target region data associated with the type label. In a particular embodiment, the endoscopic inspection method 600 further comprises: the training module associating the first image data and/or the second image data with a type label according to a second determination instruction; and the training module training the convolutional neural network module by means of the first image data and/or the second image data associated with the type label.

Hence, the endoscopic inspection system and the method thereof of the present invention are described in the above description and drawings. It should be understood that each particular embodiment of the present invention is for illustrative purpose only, and various changes can be made without departing from the scope and spirit of the claims of the present invention, and should fall within the scope of the present invention. Therefore, each particular embodiment described in the description is not intended to limit the present invention, and the scope and spirit of the present invention are disclosed in the following claims.

LIST OF REFERENCE NUMERALS

100 Endoscopic inspection system
110 Database

120 Processor
130 Switchable light source device
140 Endoscope device
150 Display device
210 Database
220 Processor
222 Training module
224 Convolutional neural network module
352 First image data
354 Second image data
356 First image data
358 Second image data
452 White light image data
454 NBI light image data
552 White light image data
554 NBI light image data
600 Endoscopic inspection method
610 Step
620 Step
630 Step
640 Step
650 Step
660 Step
670 Step
Deposit of Biological Material
None

What is claimed is:

1. An endoscopic inspection system, comprising:
  a switchable light source device for alternately providing first illumination light and second illumination light to illuminate an inspection location;
  an endoscope device for acquiring first image data of the inspection location under the illumination of the first illumination light and acquiring second image data of the inspection location under the illumination of the second illumination light;
  a processor communicatively connected to the switchable light source device and the endoscope device, wherein the processor determines, according to the first image data and/or the second image data, whether the first image data and/or the second image data contains an abnormal region, and further generates determination data associated with the first image data and/or the second image data; and
  a display device communicatively connected to the processor for displaying the first image data and the second image data respectively according to a first display instruction and a second display instruction of the processor;
  wherein the switchable light source device alternately provides the first illumination light and the second illumination light at a switching frequency greater than 30 Hz.

2. The endoscopic inspection system of claim 1, wherein the first illumination light is white light, and the second illumination light is narrow band imaging (NBI) blue light or NBI green light.

3. The endoscopic inspection system of claim 1, wherein if the processor determines that the first image data and/or the second image data contains an abnormal region, the display device is instructed to mark the abnormal region on the first image data and/or the second image data according to the determination data.

4. The endoscopic inspection system of claim 3, wherein the determination data comprises probability data, and when marking the abnormal region on the first image data and/or the second image data, the display device displays the probability data on the first image data and/or the second image data at the same time.

5. The endoscopic inspection system of claim 1, wherein the determination data comprises a type label, and the type label is associated with the first image data, the second image data, or the abnormal region.

6. The endoscopic inspection system of claim 1, wherein if the processor determines that the first image data and/or the second image data contains an abnormal region, the processor issues an alert signal.

7. The endoscopic inspection system of claim 1, wherein the processor comprises a convolutional neural network module, and the processor determines whether the first image data and/or the second image data contains an abnormal region by means of the convolutional neural network module, and further generates the determination data.

8. The endoscopic inspection system of claim 7, wherein the processor comprises a training module, and the training module trains the convolutional neural network module by means of a plurality pieces of training data; wherein each of the plurality pieces of training data is associated with a type label.

9. The endoscopic inspection system of claim 7, wherein the processor comprises a training module, and the training module acquires target region data from the first image data and/or the second image data according to a control instruction; wherein the training module associates the target region data with a type label according to a first determination instruction; wherein the training module trains the convolutional neural network module by means of the target region data associated with the type label.

10. The endoscopic inspection system of claim 7, wherein the processor comprises a training module, and the training module associates the first image data and/or the second image data with a type label according to a second determination instruction; wherein the training module trains the convolutional neural network module by means of the first image data and/or the second image data associated with the type label.

11. An endoscopic inspection method, comprising:
  alternately providing, by a switchable light source device, first illumination light and second illumination light to illuminate an inspection location;
  acquiring, by an endoscope device, first image data of the inspection location under the illumination of the first illumination light, and acquiring second image data of the inspection location under the illumination of the second illumination light;
  determining, according to the first image data and/or the second image data by a processor communicatively connected to the switchable light source device and the endoscope device, whether the first image data and/or the second image data contains an abnormal region, and further generating determination data;
  associating, by the processor, the determination data with the first image data and/or the second image data; and
  displaying, by a display device communicatively connected to the processor, the first image data and the second image data respectively according to a first display instruction and a second display instruction of the processor;
  wherein the switchable light source device alternately provides the first illumination light and the second illumination light at a switching frequency greater than 30 Hz.

12. The endoscopic inspection method of claim 11, wherein the first illumination light is white light, and the second illumination light is narrow band imaging blue light or narrow band imaging green light.

13. The endoscopic inspection method of claim 11, further comprising: if the processor determines that the first image data and/or the second image data contains an abnormal region, instructing, by the processor, the display device to mark the abnormal region on the first image data and/or the second image data according to the determination data.

14. The endoscopic inspection method of claim 13, wherein the determination data comprises probability data, and when marking the abnormal region on the first image data and/or the second image data, the display device displays the probability data on the first image data and/or the second image data at the same time.

15. The endoscopic inspection method of claim 11, wherein the determination data comprises a type label, and the type label is associated with the first image data, the second image data, or the abnormal region.

16. The endoscopic inspection method of claim 11, further comprising: if the processor determines that the first image data and/or the second image data contains an abnormal region, issuing, by the processor, an alert signal.

17. The endoscopic inspection method of claim 11, wherein the processor comprises a convolutional neural network module, and the processor determines whether the first image data and/or the second image data contains an abnormal region by means of the convolutional neural network module, and further generates the determination data.

18. The endoscopic inspection method of claim 17, further comprising: training, by a training module of the processor, the convolutional neural network module by means of a plurality pieces of training data; wherein each of the plurality pieces of training data is associated with a type label.

19. The endoscopic inspection method of claim 17, further comprising:
  acquiring, by a training module of the processor, target region data from the first image data and/or the second image data according to a control instruction;
  associating, by the training module, the target region data with a type label according to a first determination instruction; and
  training, by the training module, the convolutional neural network module by means of the target region data associated with the type label.

20. The endoscopic inspection method of claim 17, further comprising:
  associating, by a training module of the processor, the first image data and/or the second image data with a type label according to a second determination instruction; and
  training, by the training module, the convolutional neural network module by means of the first image data and/or the second image data associated with the type label.

* * * * *